United States Patent
Cecconi et al.

(10) Patent No.: US 8,303,560 B2
(45) Date of Patent: Nov. 6, 2012

(54) ELASTIC MATERIAL COATED IN FIBERS, A DIAPER COMPRISING SAID ELASTIC MATERIAL AND A METHOD FOR THE PRODUCTION THEREOF

(75) Inventors: Riccardo Cecconi, Prato (IT); Barbara Bulleri, Pistoia (IT); Chiara Allegrini, Lucca (IT); Stefano Muroni, Pistoia (IT); Claudio Giacometti, Pistoia (IT)

(73) Assignee: Fintex & Partners Italia S.p.A., Pistoria (IT)

( * ) Notice: Subject to any disclaimer, the term of this patent is extended or adjusted under 35 U.S.C. 154(b) by 911 days.

(21) Appl. No.: 11/911,153

(22) PCT Filed: Apr. 7, 2006

(86) PCT No.: PCT/IT2006/000236
§ 371 (c)(1),
(2), (4) Date: May 22, 2008

(87) PCT Pub. No.: WO2006/109341
PCT Pub. Date: Oct. 19, 2006

(65) Prior Publication Data
US 2009/0221982 A1     Sep. 3, 2009

(30) Foreign Application Priority Data
Apr. 11, 2005 (IT) .................. FI2005A0068

(51) Int. Cl.
*A61F 13/15* (2006.01)

(52) U.S. Cl. .................. 604/385.22; 604/365; 604/372; 604/373; 604/374; 604/378; 604/385.101; 604/384

(58) Field of Classification Search .................. 604/365, 604/374, 378, 385.101, 384, 373, 372, 385.22
See application file for complete search history.

(56) References Cited

U.S. PATENT DOCUMENTS

| | | |
|---|---|---|
| 3,098,755 A | 7/1963 | Barth et al. |
| 3,896,802 A | 7/1975 | Williams |
| 5,422,172 A | 6/1995 | Wu |
| 6,028,017 A | 2/2000 | Curtin et al. |
| 6,255,236 B1 | 7/2001 | Cree et al. |
| 6,537,930 B1 | 3/2003 | Middlesworth et al. |
| 2003/0009144 A1 | 1/2003 | Tanzer et al. |
| 2003/0022582 A1 | 1/2003 | Cree et al. |
| 2003/0084986 A1 | 5/2003 | Cree et al. |
| 2003/0105446 A1 | 6/2003 | Hutson et al. |
| 2003/0216704 A1 | 11/2003 | George |
| 2004/0055692 A1* | 3/2004 | Abrams .................. 156/72 |

FOREIGN PATENT DOCUMENTS

| | | |
|---|---|---|
| CH | 604 580 | 9/1978 |
| EP | 0 737 462 A1 | 10/1996 |
| JP | 2001-198997 | 7/2001 |

* cited by examiner

*Primary Examiner* — Jacqueline F. Stephens
(74) *Attorney, Agent, or Firm* — McGlew and Tuttle, P.C.

(57) ABSTRACT

The composite material comprises an elastic film (F), made of polymer material, and a coating made of flocked fibers (13) on at least one face. The fibers are fixed to the film by a layer (C) of bonding material.

31 Claims, 3 Drawing Sheets

ELASTIC MATERIAL COATED IN FIBERS, A DIAPER COMPRISING SAID ELASTIC MATERIAL AND A METHOD FOR THE PRODUCTION THEREOF

TECHNICAL FIELD

The present invention relates to innovations in the field of hygienic products production, in particular baby diapers, incontinence diapers and the like.

BACKGROUND OF THE INVENTION

In baby diapers and other similar products, elastic components are used to adapt the article to the body shape of the user.

For this purpose polymer films with elastic properties are used, i.e. polymer films that can be stretched and deformed by elongation remaining in the substantially elastic range, so that when the film is released it returns approximately to its original configuration, or has a limited permanent deformation, typically within 10% of the initial length after 3 elongation cycles at 80%.

From a film of this type elastic strips are produced which are applied to the diaper to give it the necessary fit and to allow it to be adapted or applied to the user. In baby diapers elastic films of this type are used to produce the closing tabs of the diaper. In "training pants" used today to facilitate the passage from using a diaper to using normal pants, strips of elastic film are used to form the side bands of the article, which is worn like normal pants, but has the structural and functional properties of a diaper. In particular, in this application the article has large surfaces made of elastic polymer film.

As contact of the polymer film with the skin would be unpleasant and, especially in use in baby diapers, might give rise to phenomena of cutaneous irritation, systems have been studied to coat the polymer film with textile fibers. The coating in textile fibers also has the function of giving the product a better "handle", not only for the person wearing it, but also for the person who handles it. Fiber coatings are therefore used also on elastic films used for components of the diaper that do not come into contact with the skin of the user.

U.S. Pat. No. 5,422,172 discloses a laminate formed of an elastic film bonded to a layer of nonwoven and a relative method of production. The polymer film is extruded directly in the nip of a calender, through which one or two card webs are fed. The fibers are bonded directly to the extruded film. This process requires complex machinery, as the film must be extruded directly at the mouth of the calender. Moreover, when the product thus obtained is pulled and elongated this causes breakage of the fibers.

According to other techniques the web of fibers is bonded to a preformed film. This type of product has not proved to be satisfactory, as if the nonwoven is applied to the polymer film holding the latter in the stretched position, when the laminate obtained is released and the film returns to its non-elongated position, the nonwoven becomes wrinkled. Moreover, in these techniques the film is elongated, i.e. pre-stretched in machine direction (MD), i.e. in the direction parallel to the direction of feed of the material. On the other hand, when the semi-finished product is used to produce absorbent articles or garments (such as diapers or the like), elasticity in a cross direction (CD), or prevalently cross direction, is generally required. This is because in the conformation phase of the diaper, if the elastic product is fed aligned with the diaper, the production speed is much greater than the speed which would be achieved if the elastic band were to be fed in the cross direction and then rotated.

If the film is laminated to the nonwoven web without first having been stretched and elongated, the nonwoven obstructs elongation of the film during use and the fibers can detach or break. Alternatively, elastic nonwovens would have to be used, but these have a high cost.

US-A-2003/0105446 describes a composite laminated product comprising an intermediate polymer film laminated to two webs of fibers. Also in this case the film is extruded directly in the machine that performs lamination with at least one of the two layers of fibers. The composite product is then subjected to elongation in the elastic range to break the fibers and give the finished article the elasticity of the film. The possibility of perforating the film is also described. This production process is complex and unsatisfactory due to breakage of the fibers, which on the other hand is necessary to obtain a semi-finished product with adequate elastic properties at the end of the production line.

Further methods for producing an elastic film and fiber laminate are described in US-A-2003/0084986 and in U.S. Pat. No. 6,537,930, US-A-2003/0022582 and in U.S. Pat. No. 6,255,236.

EP-B-0737462 describes a composite material composed of a non-elastic polymer film on which a layer of flocked fibers is formed. This material is used in particular as a topsheet in feminine sanitary napkins. The film has a perforation to allow the passage of body fluids.

OBJECTS AND SUMMARY OF THE INVENTION

An object of the present invention is the implementation of a new method for producing laminates comprising an elastic film, particularly suitable as elastic components in baby diapers, incontinence diapers and other hygienic absorbent products.

According to a different aspect, an object of the present invention is to produce an absorbent article, in particular, although not exclusively, a baby diaper or incontinence diaper, with at least one elastic component which is easier and more pleasant to wear and which offers increased comfort and increased fit and adaptability to the body shape of the user.

According to yet another aspect, an object of the invention is to produce an elastic laminate article, comprising an elastic film and a coating of textile fiber, particularly suitable and efficacious as component of hygienic napkins and baby diapers or incontinence diapers or for similar products.

Substantially, according to a first aspect the invention relates to a composite material comprising an elastic film, made of polymer material, and a coating made of fibers on at least one face of said film, wherein the coating made of fibers is formed of flocked fibers.

Therefore, contrary to conventional elastic films, according to the invention the coating is obtained with very short fibers, which are bonded to the film being positioned orthogonally to the surface of the film. In this way the fiber does not form an obstruction to elongation of the film, does not break when the film is elongated and does not form wrinkles if the film is elongated and coated with the fibers in conditions of elastic elongation. However, flocking preferably takes place without subjecting the film to pre-stretching.

Advantageously, the fibers are bonded to the film with a bonding material, such as a polymerizable resin or an adhesive. This material has the property of having an elasticity of its own when dried, cross-linked or polymerized. Alternatively, it is possible to use materials which, once applied to the polymer film, give rise to a discontinuous distribution, typically in the form of a grid, rather than in the form of a continuous layer. Hot melt adhesives with this property are known and used in the production of absorbent articles. As the adhesive does not deposit in the form of a continuous film or layer, but is microporous, the fragments of adhesive form small islands, which can also be in contact with one another, to which the fibers bond. Therefore, stretching of the film in general causes extremely modest deformation of the adhesive/fiber assembly.

In this way the bonding layer, whether a resin or an adhesive, follows the elongation of the composite material and returns to its initial condition, recovering elastic deformation, without forming wrinkles and breaking.

The bonding material, being applied in a fluid or paste state, has substantially isotropic elastic properties, i.e. equal in all directions. On the other hand, the film to which the fibers are applied by flocking can have properties of elasticity differentiated in the various directions. For example, it can have increased elasticity in machine direction, i.e. in the direction of feed of the film, than in cross direction. Conversely, and preferably, the film can have properties of elasticity substantially comparable in the two directions, cross and machine. This simplifies its subsequent use as semi-finished product for the production of finished articles, such as baby diapers, training pants for children or the like.

Elastic film is intended as a film which, in the principal direction of elongation or in several principal directions of elongation (e.g. in machine direction and cross direction) has a capacity of deformation by elongation and subsequent recovery of the original length adequate for use as a component in garments such as baby diapers or the like. Typically, according to an advantageous embodiment, the elasticity of the plastic film and of the bonding material of the fibers is such that the composite material can undergo a fatigue cycle to 80% of elongation, recording a maximum permanent deformation of 20% or less.

Possible elastic polymer films usable and commercially available are the following:

A) Polyurethane UE30 S MATT L
Supplier: Chiorino Spa
Via S. Agata 9
13900 Biella Italy
B) Elastic bubble film AB 1312/99
Supplier: RKW AG
Rheinische Kunststoffwerke
Alkorstrasse 6
83512 Wasserburg/Inn (GERMANY)
C) Elastic film Flexaire 100
Supplier: Tredegar Industries Inc.
1100 Boulders Parkway
Richmond Va. 23225
D) Elastic film EXXON
Supplier: ExxonMobil Chemical Europe
Bayton Technology & Engineering Complex
5200 Bayway Drive
Baytown Tex. 77520-2101
E) Elastic film HB001 XC001 8(110-40 µm)
Supplier: Lo Presti
Via XX Settembre, 30
22100 Como More generally, polymer films with suitable elastic properties can be based on addition and condensation polymers, such as polyolefins, ethylene-polypropylene copolymers, but also films based on styrene-butadiene or polyurethane. Examples of other materials made of elastic synthetic resin are indicated in the patent literature cited in the introductory part of this description.

Micro-perforated elastic films, which offer breathability, can also be used.

Adhesives usable as elastic material to bond the fibers can be based on polyolefins or synthetic rubbers. Examples of commercially available adhesives with elastic properties suitable for application in the present invention or capable of forming a porous or grid-like, i.e. discontinuous, distribution, for the objects indicated above, are the following:

Sanicare HM 6700 (polyolefin based hot melt adhesive)
Sanicare HM 521 VP (polyolefin based hot melt adhesive)
Sanicare HM 6540 (rubber based elastic hot melt adhesive)
ECOMELT H 339 UV (rubber based elastic hot melt adhesive)
Supplier: Henkel Sanicare
40191 Düsseldorf Germany
H53 (Ethylene vinyl acetate based hot melt adhesive)
Supplier: Nuova Unicol® srl
via 1° maggio, 18
31043 Fontanelle (TV)—Italy In alternative to adhesives, polymerizable, elastic and water-foamable resins can be used, so that they can be spread to form a layer or coating on the film. These are then cross-linked in the oven. Possible elastic resins suitable for this specific application are the following:

1) ACRONAL 579S: thermal cross-linking resin based on acrylonitrile copolymers and acrylic esters (supplier BASF—Germany)

2) CRILAT 4710 and 4735: styrene-acrylic resins (supplier VINAVIL)

3) PRIMAL NW185 and PRIMAL ECO36: thermal cross-linking acrylic resins (supplier Acril Nova s.r.l.—Italy)

According to a possible embodiment, the polymer film has a thickness ranging from 5 to 400 µm, preferably from 20 to 200 µm, and even more preferably from 30 to 70 µm. The fiber can be applied to the surface of the film or to each surface of the film with a quantity of fibers per surface unit ranging from 2 g/m$^2$ to 100 g/m$^2$, preferably from 5 g/m$^2$ to 40 g/m$^2$ and even more preferably from 7 to 20 g/m$^2$. The quantity of bonding material of the fibers can range from 1 to 30 g/m$^2$, preferably from 5 to 10 g/m$^2$ on each face, the weight being determined after drying or cross-linking.

The fibers can advantageously have a count ranging from 0.3 to 3.3 dtex, and a length ranging from 0.2 and 1.5 mm. The fibers can be viscose, polyester, polypropylene, two-component, cotton, wool, polyethylene, PLA or biodegradable fibers in general.

The invention further relates to an absorbent article comprising at least one component formed with a composite material as defined above.

Further advantageous characteristics and embodiments of the invention are indicated in the appended claims.

BRIEF DESCRIPTION OF THE DRAWINGS

The invention will be better understood by following the description and accompanying drawing, which shows a non-limiting practical embodiment of the invention. In the drawing.

DETAILED DESCRIPTION OF AN EMBODIMENT OF THE INVENTION

Figure 1:
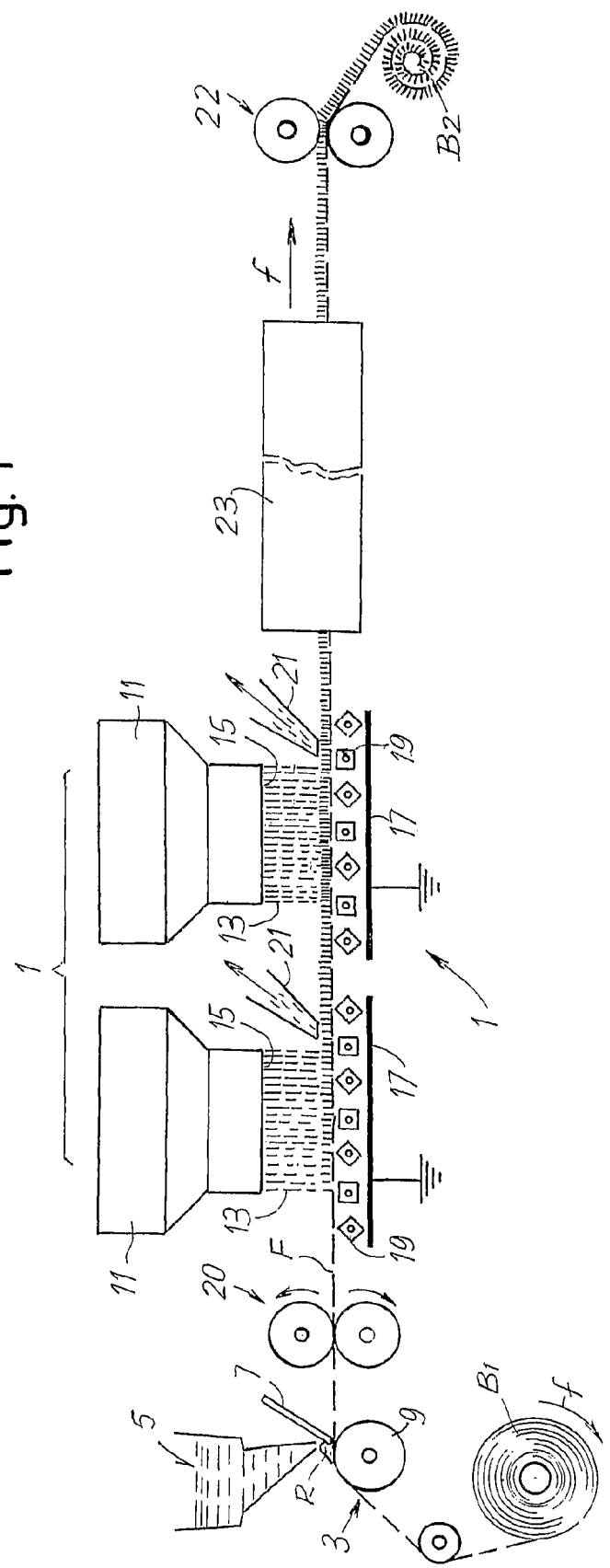
FIG. 1 shows a schematic side view of a possible production line of the material according to the invention.

FIG. 1 shows, very schematically, a system for producing a flocked elastic film according to a first embodiment. Systems of this type are per se known and are commonly used to produce imitation velvets. A system of this type can be adapted to produce the film according to the present invention. The structure is described briefly here, without going into the constructional details, known to those skilled in the art.

B1 indicates a reel of elastic film F to be treated, which is unwound according to the arrow f and fed to a flocking machine 1. The film can have elasticity in machine direction (MD), i.e. in the direction of feed and preferably has an elasticity in cross direction (CD).

Positioned upstream of the flocking machine 1 is a coating station 3, in which a hot melt coating system 5 or another suitable means distributes a hot melt adhesive R or a polymerizable resin R on the upper face of the film F, which forms a bonding layer of the flocked fibers on the film. The resin or adhesive, which forms the bonding layer, is a material which at the end of the process is elastic. Position downstream of the coating unit 5 is a doctor 7 which distributes the resin or adhesive R on the film F. The doctor can have a smooth edge positioned at a predetermined distance from the surface of the film and parallel thereto, so that a uniform layer with a constant thickness is spread on the film. On the other hand, a doctor with a toothed profile can be provided. By positioning the doctor so that the teeth touch the surface of the film F, the latter is spread with strips of resin of a uniform thickness, approximately equivalent to the height of the teeth and having a width in the direction crosswise to film movement equivalent to the length of the lowered portions of the doctor, between one tooth and the subsequent tooth. The doctor 7 cooperates with a counter-pressure roller 9 or with another suitable counter-pressure means, such as a conveyor belt or the like on which the film F rests.

The flocking machine shown in FIG. 1 has two stations, but it would also be possible to use a single station or more than two stations. Each station has a metering device 11 from which an adjustable quantity of fibers 13 is delivered on the film F below. The zone in which the fibers 13 fall is immersed in an electrostatic field with force lines directed vertically and perpendicular to the film. The electrostatic field is obtained with two electrodes 15 and 17 positioned above and below the film F. In this way the fibers bond to the layer of resin spread on the upper face of the film, oriented according to the force lines of the electrostatic field.

A vibrator 19 positioned below the film makes this vibrate at high frequency to allow correct distribution of the fibers and remove fibers that are not correctly bonded to the resin. These are sucked up by a suction device 21.

Downstream of the flocking machine the film is made to pass through a station 23 which can vary in type depending on the nature of the material R applied to bond the fibers. If this material is a hot polymerizable resin, the unit or station 23 can be an oven. On the other hand, and preferably, when this bonding material is a hot melt resin, the unit 23 is a cooling unit, where the hot melt adhesive is cooled until it has hardened completely. The film delivered from the oven is then rewound on a reel B2.

In the example illustrated two pairs of rollers 20, 22 are provided, at least one of which has a motorized roller, to hold the film F taut in machine direction, and then apply the flocked fibers to the taut and elongated polymer film. However, this is not binding, and the film can be fed through the flocking machine 1 in relaxed conditions, i.e. not elongated. According to a preferred embodiment, the film F is fed in relaxed mode, i.e. not pre-stretched.

Figure 2:
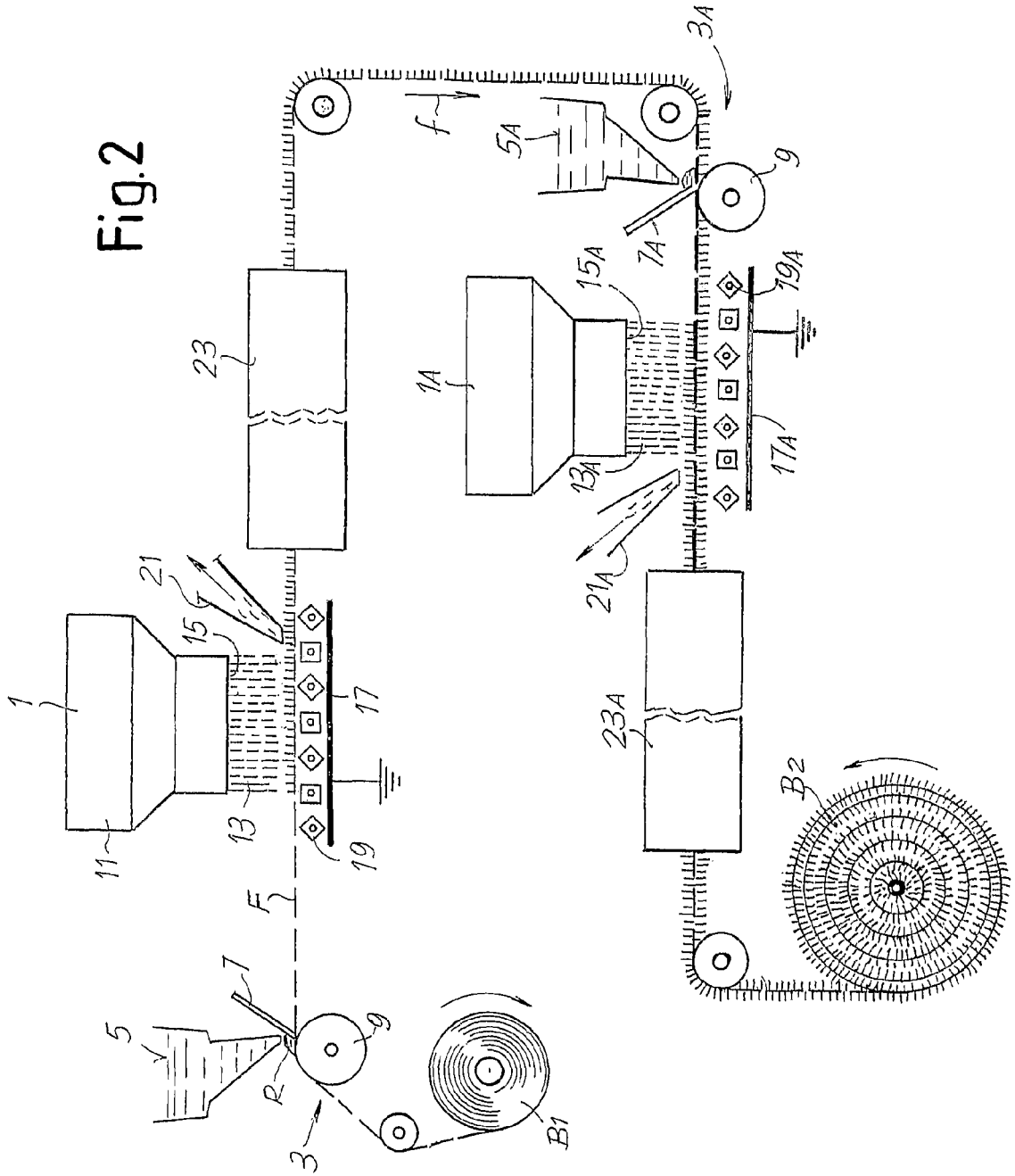
FIG. 2 shows a schematic side view of a possible production line in a further embodiment.

FIG. 2 shows a variant of embodiment with respect to the line in FIG. 1. The same numbers indicate parts that are the same or correspond to those in FIG. 1. In this case two flocking machines are provided, indicated with 1 and 1A. Each of them is single. The first flocking machine is preceded and followed by the same elements described with reference to FIG. 1. Positioned downstream of the oven 23 is a coating station 3A with a nozzle or unit for application of a hot melt adhesive, indicated as a whole with 5A, which applies the resin or adhesive on the face of the film F opposite the one flocked in the flocking machine 1. Positioned downstream of the unit 5A is a doctor 7A which distributes the adhesive or resin uniformly before the film F enters the second flocking machine 1A, configured in the same way as the flocking machine 1. Positioned downstream of the flocking machine 1A is a unit 23A having a similar function as that of the unit 23. The film F is thus flocked on both faces and is rolled on the reel B2.

Figure 3:
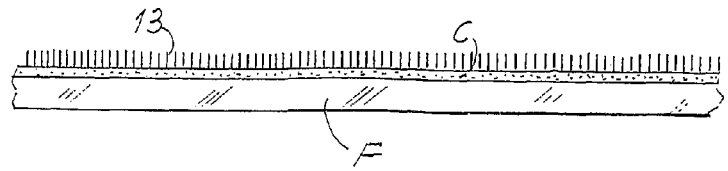
FIGS. 3 and 4 show schematic sections of a portion of material produced with the line in FIG. 1, in a relaxed position and in a position elongated under stress.
Figure 4:
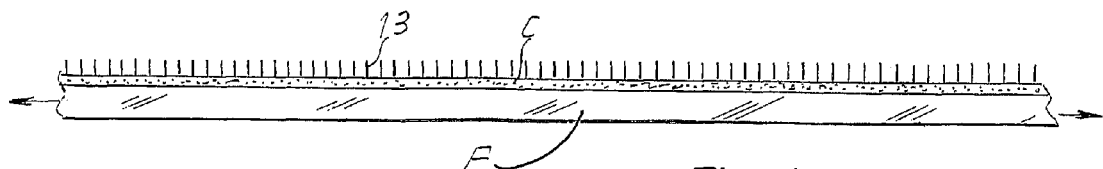

FIGS. 3 and 4 schematically show a portion of film obtained with the production line in FIG. 1 in two arrangements, relaxed and taut respectively. The fibers 13 are positioned approximately orthogonal to the extension of the film. The film F and the resin or adhesive R applied thereon have elastic properties, so that by subjecting the film to stretching stress (FIG. 3B) it is elongated and the fibers 13 are distanced from one another, but remain undamaged and bonded correctly. Moreover they maintain a substantially uniform distribution if elongation of the elastic film and relative adhesive is uniform.

Figure 5:
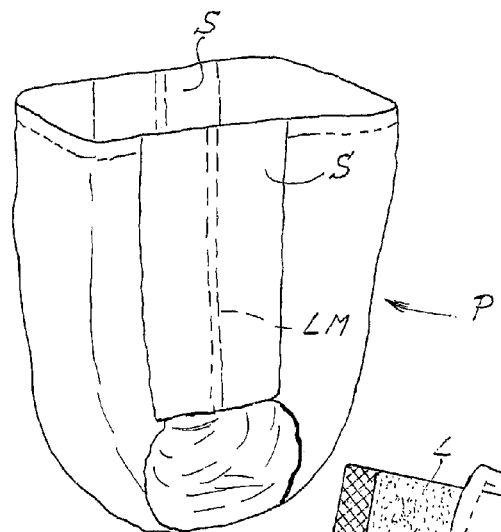
FIG. 5 shows training pants produced using the material according to the invention.

FIG. 5 shows a possible application of a flocked elastic film obtained according to the method described above to so-called training pants. The training pants are indicated as a whole with P. They have, in a per se known way, side bands or strips S, which fasten round the waist of the child. In the example shown the side bands or strips S are each produced with two portions of flocked film F joined together along an intermediate line LM. Joining of the portions of film can take place by heat bonding, ultrasound, gluing or in another known way. The flocked fibers 13 can be made of thermoplastic material and therefore even if applied in the overlap and bonding zone of the two portions of film forming the band S, they do not obstruct bonding. Alternatively, also using viscose fibers, the coating of the film, i.e. the density of the fibers 13 on the film, is such to allow bonding.

Alternatively, according to an advantageous embodiment, the training pants P can have an elastic band which surrounds the entire opening of the garment and which encircles the child around the waist. In this case a single strip of flocked elastic film can be bonded along the head and tail edges to form an annular strip or band.

Figure 6:
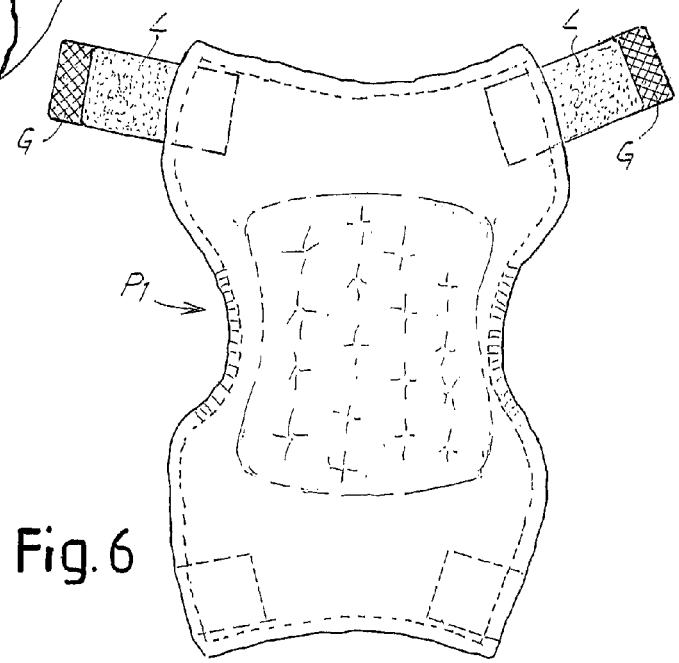
FIG. 6 shows a diaper produced with components produced with a material according to the invention.

FIG. 6 shows a different use of the flocked elastic film according to the invention. In this case, the garment to which the flocked elastic film is applied is a diaper P1 with two elastic tabs L applied to the ends of the back part of the diaper. These tabs are made with the flocked elastic film according to the invention and are provided (in a per se known way) with portions of bonding material G, made of Velcro®, to close the tabs by adhesion to the front portion of the diaper.

It is understood that the drawing only shows possible embodiments and of use of the invention, which can vary in forms and arrangements without however departing from the scope of the concept on which the invention is based. Any reference numerals in the appended claims are provided purely to facilitate reading in the light of the preceding description and do not limit the scope of protection.

The invention claimed is:

1. A composite material comprising an elastic film, made of polymer material, and a coating made of flocked fibers fixed to at least one face of said film, by a layer of bonding material, wherein said bonding material is distributed discontinuously and that the quantity of fibers per surface unit on said at least one face ranges from 5 g/m² to 40 g/m².

2. Composite material as claimed in claim 1, wherein said layer of bonding material has elastic properties.

3. Composite material as claimed in claim 2, which has elasticity prevalently in the direction crosswise to machine direction.

4. Composite material as claimed in claim 2, which has elasticity in two directions orthogonal to each other.

5. Composite material as claimed in claim 1, which has elasticity prevalently in the direction crosswise to machine direction.

6. Composite material as claimed in claim 1, which has elasticity in two directions orthogonal to each other.

7. Composite material as claimed in claim 1, having a permanent deformation equal to or less than approximately 20% after a stress cycle with elongation at 80% of the original length thereof.

8. Composite material as claimed in claim 1, wherein said polymer film has a thickness ranging from 5 to 400 μm, preferably from 20 to 200 μm, and even more preferably from 30 to 70 μm.

9. Composite material as claimed in claim 1, further comprising on said at least one face a quantity of fibers per surface unit on at least one face ranging from 7 g/m² to 20 g/m².

10. Composite material as claimed in claim 1, wherein a quantity of fiber bonding material ranging from 1 to 30 g/m², preferably from 5 to 10 g/m² on each face, is applied to said at least one face, the weight being determined on the dried or cross-linked product.

11. Composite material as claimed in claim 1, wherein said fibers are thermoplastic fibers.

12. Composite material as claimed in claim 1, wherein said fibers have a count ranging from 0.3 to 3.3 dtex.

13. Composite material as claimed in claim 1, wherein said fibers have a length ranging from 0.2 to 1.5 mm.

14. Composite material as claimed in claim 1, further comprising a coating of flocked fibers on both faces.

15. Composite material as claimed in claim 1, wherein said elastic film is produced with a polymer chosen from the group comprising: polyolefins, ethylene-propylene copolymers, styrene-butadiene, polyurethane.

16. Composite material as claimed in claim 1, wherein said bonding layer is formed of an elastic polymerized resin.

17. Composite material as claimed in claim 16, wherein said elastic polymerized resin forming the bonding layer is chosen from the group comprising: resins based on acrylonitrile copolymers and acrylic esters; styrene-acrylic resins; acrylic thermal cross-linking resins.

18. Composite material as claimed in claim 1, wherein said bonding material of the flocked fibers is an adhesive.

19. Composite material as claimed in claim 18, wherein said adhesive is a hot melt adhesive.

20. Composite material as claimed in claim 18, wherein said adhesive is based on polyolefins or synthetic rubbers.

21. Composite material as claimed in claim 1, having a permanent deformation equal to or less than approximately 20% after a stress cycle with elongation at 80% of the original length thereof.

22. An absorbent article comprising at least one component formed with a composite material including an elastic film, made of polymer material, and a coating made of flocked fibers fixed to at least one face of said film, by a layer of bonding material, wherein said bonding material is distributed discontinuously and that the quantity of fibers per surface unit on said at least one face ranges from 5 g/m² to 40 g/m².

23. A baby diaper comprising elastic closing tabs, wherein said elastic tabs have at least one portion made with a composite material including an elastic film, made of polymer material, and a coating made of flocked fibers fixed to at least one face of said film, by a layer of bonding material, wherein said bonding material is distributed discontinuously and that the quantity of fibers per surface unit on said at least one face ranges from 5 g/m² to 40 g/m².

24. Training pants comprising at least one elastic band at the height of the waist, produced at least in part with a portion of composite material including an elastic film, made of polymer material, and a coating made of flocked fibers fixed to at least one face of said film, by a layer of bonding material, wherein said bonding material is distributed discontinuously and that the quantity of fibers per surface unit on said at least one face ranges from 5 g/m² to 40 g/m².

25. A composite material comprising:
an elastic film having a surface and another surface;
a layer of bonding material arranged discontinuously on said surface of said elastic film;
a coating made of flocked fibers fixed to said surface of said elastic film by said layer of bonding material.

26. A composite material in accordance with claim 25, wherein:
said coating of said fibers arranged on said face in a quantity ranging from 5 g/m² to 40 g/m²;
said elastic film is made of polymer material.

27. A composite material in accordance with claim 25, wherein:
said layer of bonding material has elastic properties comparable to said elastic film.

28. A composite material in accordance with claim 25, wherein:
said elastic film has elasticity in two directions orthogonal to each other.

29. A composite material in accordance with claim 28, wherein:
said flocked fibers are arranged orthogonal to said surface of said elastic film;
said a layer of bonding material is arranged in a grid pattern on said surface of said elastic film.

30. A composite material in accordance with claim 25, further comprising:
another layer of bonding material distributed discontinuously on said another surface of said elastic film;
another coating made of flocked fibers fixed to said another surface of said elastic film by said another layer of bonding material.

31. A composite material in accordance with claim 25, wherein:
said flocked fibers are arranged orthogonal to said surface of said elastic film;
said a layer of bonding material is arranged in a grid pattern on said surface of said elastic film.

* * * * *